United States Patent [19]

Green

[11] 4,084,902

[45] Apr. 18, 1978

[54] METHOD AND APPARATUS FOR PRODUCING A SUSPENSION OF BIOLOGICAL CELLS ON A SUBSTRATE

[76] Inventor: James Edmond Green, P.O. Box 734, Fayetteville, Tenn. 37334

[21] Appl. No.: 708,878

[22] Filed: Jul. 26, 1976

[51] Int. Cl.² .............................................. G01N 1/10
[52] U.S. Cl. ........................................, 356/38; 356/39; 356/103; 356/111; 356/196
[58] Field of Search ..................... 356/36, 38, 39, 103, 356/104, 109, 111, 196

[56] References Cited

U.S. PATENT DOCUMENTS

| | | | |
|---|---|---|---|
| 3,783,296 | 1/1974 | Bleuins | 356/111 |
| 3,827,805 | 8/1974 | Mansfield et al. | 356/73 |
| 3,955,890 | 5/1976 | Bessis et al. | 356/103 |

Primary Examiner—John K. Corbin
Assistant Examiner—R. A. Rosenberger
Attorney, Agent, or Firm—Richard J. Birch

[57] ABSTRACT

A method and apparatus for producing a suspension of biological cells of a predetermined density (or cell spacing) on a substrate. Illumination incident upon the cell suspension is modified by the cell suspension to form a characteristic diffraction pattern. A portion of the diffraction pattern is detected at at least one off-axis location with respect to the axis of the incident illumination. The thickness of the cell suspension is reduced and the changes in the characteristic cell diffraction pattern are observed until a predetermined pattern is achieved, at which point the reduction in thickness is terminated.

36 Claims, 12 Drawing Figures

METHOD AND APPARATUS FOR PRODUCING A SUSPENSION OF BIOLOGICAL CELLS ON A SUBSTRATE

BACKGROUND OF THE INVENTION

This invention relates to a method and apparatus for producing a cell suspension layer of a predetermined cell density (or cell spacing) on a substrate, and more particularly, to a system which senses the cell density on the substrate and automatically terminates the thickness reduction when a predetermined cell density is achieved.

In many areas of medical and biological work cell monolayers are visually examined to derive diagnostic information about the patient. Common examples of this are the examination of the blood film in the differential blood cell count and the examination of cervical cells in the Pap test. The classical manual methods for preparing cell monolayers for examination unfortunately produce cell densities of greatly varying thicknesses. Recently a method has been develloped which allows a very uniform monolayer of cells to be produced from a suspension of cells in a liquid.

U.S. Pat. Nos. 3,577,267 by Preston et al and 3,705,048 by Staunton describe two apparati which implement a method that is generally known as "spinning," in which a microscope slide or other carrier substrate is wetted with an excess of the cell suspension and spun rapidly. The excess cell suspension is quickly spun off by centrifugal force and a uniform monolayer forms on the substrate. When the monolayer has achieved the proper cell density, spinning is stopped. Because of the variations of properties of naturally occurring biological cell suspensions, the optimum spin time to produce a monolayer with ideal cell separation is not constant, but instead varies from sample to sample. In the two abovementioned patents, it is necessary to determine the optimum spin time by trial and error for each sample. The empirical determination of optimum spin times greatly reduce the usefulness of the method for high volume tests.

In U.S. Pat. No. 3,827,805, Mansfield et al, there is described a control system for a blood film spinner which overcomes the necessity for the trial and error determination of the optimum spin time. In this apparatus a beam of light is focused through the transparent substrate and the cell suspension during the spinning operation. The reduction in the transmitted light caused by the absorption or scattering in the cell suspension is measured by a direct light detector, and the amount of scattered light is summed by a large scattered light detector. The ratio of the outputs of the two detectors is compared to an exponentially decaying signal. The spinning is terminated when a predetermined relationship exists between the ratio signal and the exponentially decaying signal.

The device described by Mansfield in the aforementioned patent has several apparent shortcomings. The use of direct light as a control signal introduces inaccuracies because a reduction in direct light transmission may be caused by factors other than cell suspension thickness or cell spacing. Although the total amount of scattered light is a measure of the thickness of the cell monolayer, it can be influenced by other factors, such as, changes in the refractive index of the blood plasma relative to the refractive index of the cells. Thus, the ratio of transmitted-to-scattered light can vary for each cell spacing with the concomitant possibility of an erroneous spin time.

Similarly, the summing of all scattered light in a single scattered light sensor reduces the sensitivity of the measurement which can be achieved if the relative intensities of different parts of the pattern of scattered light are measured individually. The summing of light from all parts of the scattered light pattern can mask large changes in the proportion of light being scattered into different parts of the pattern while the total amount of scattered light remains relatively constant. This can lead to a lack of sensitivity and errors in a Mansfield device.

BRIEF SUMMARY OF THE INVENTION

In the present invention, direct light transmission is not used to detect the cell suspension thickness or cell density. In the preferred embodiment, a preselected portion of the scattered light pattern, commonly called the diffraction pattern, is sensed at two predetermined positions. Spinning is terminated when a predetermined ratio of intensities is achieved at these two positions. It is not necessary to compare these two signals to an exponentially decreasing signal as does Mansfield. The proper control of spinning parameters allows optimum cell spacing (cell density) to be achieved over a wide variety of blood samples.

It is a general object of the invention to provide an improved method and apparatus for automatically producing a uniform monolayer of suspended cells with optimum cell separation or density.

It is a specific object of the invention to provide a method and apparatus for automatically measuring the cell suspension density by observing and measuring the diffraction pattern produced by the cell suspension when it is illuminated.

These objects and other objects and features of the present invention can best be understood from a detailed description of a preferred embodiment thereof, selected for purposes of illustration and shown in the accompanying drawings, in which:

Figure 1A:
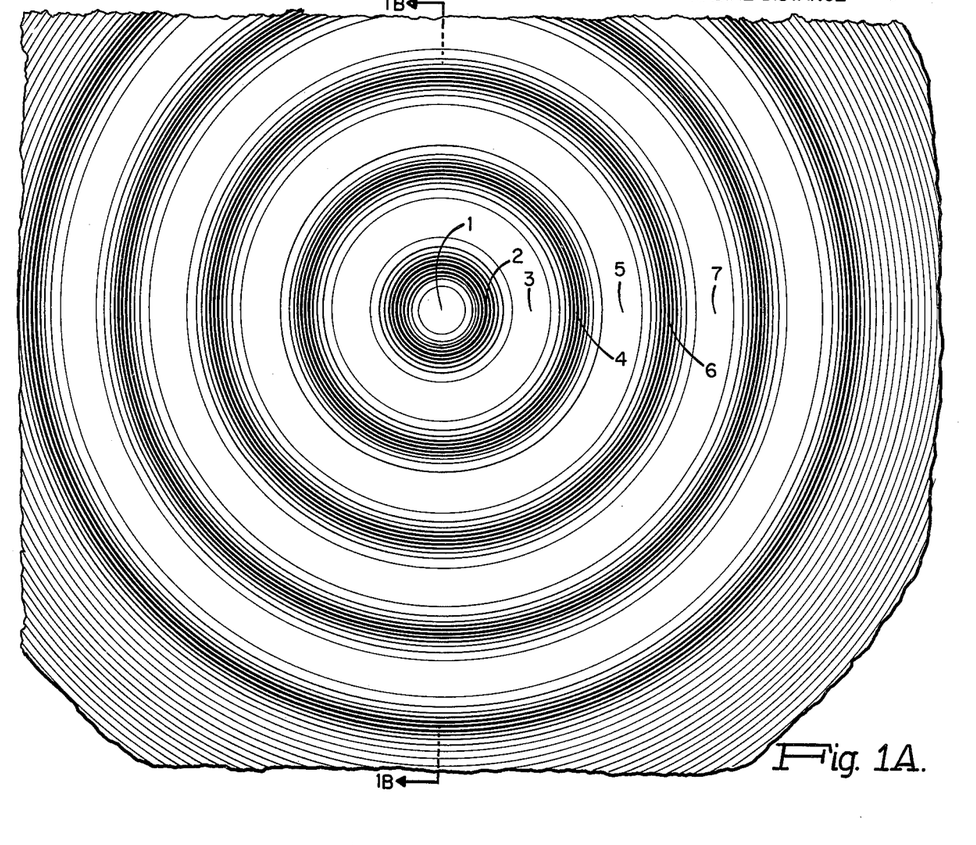
FIG. 1A is a representation of an idealized diffraction produced by a monolayer.
Figure 1B:
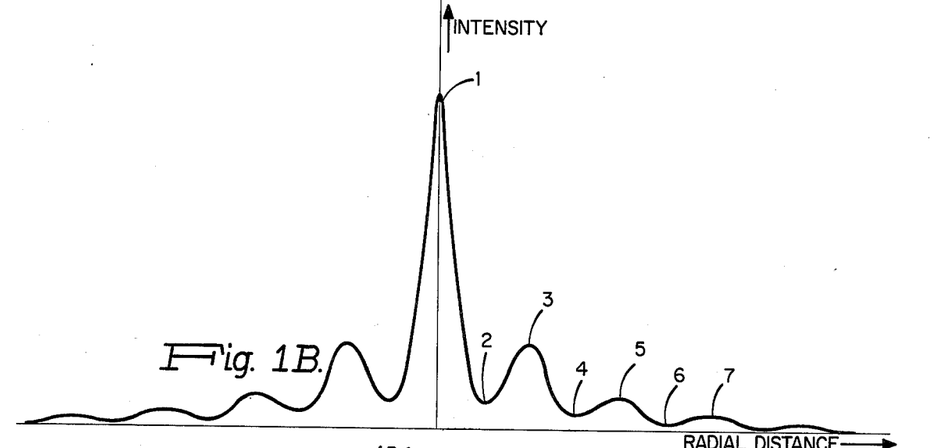
FIG. 1B is a plot of the intensity vs radial distance taken along line 1B—1B in FIG. 1A.

Turning now to the drawings, FIG. 1A is a representation of an idealized diffraction pattern produced by electro-magnetic radiation. FIG. 1B is a plot of the FIG. 1A pattern intensity, vs radial distance. Characteristically, the diffraction pattern was a bright central spot, formed on the optical axis by the transmitted incident radiation e.g. light (infrared, visible, ultraviolet). Around the central spot there are a series of circularly symetrical maxima 3, 5, 7 and minima 2, 4, 6 in the pattern which appear as a series of alternating light and dark rings. The spacing of the rings is determined by the size of and spacing between the objects producing the diffraction.

The diffraction pattern shown in FIG. 1A is an idealized pattern. In practice, on a blood film, the blood cells tend to be randomly distributed and will not have exactly uniform size. Thus, the diffraction pattern produced will not have as sharp maxima or minima as that shown in FIG. 1, and the spacing of the rings will represent an average of the diffraction ring spacings produced by the individual cell sizes and cell spacings.

In the early stages of spinning, the cells are so disordered that the individual diffraction from each cell tends to cancel out and no pattern can be seen. However, as a monolayer begins to form, the cells begin to assume a more orderly arrangement and a pattern appears. The pattern changes during the spreading process as a result of the increasing cell spacing and it tends to reach a maxium when the average cell spacing is about one cell diameter. However, particular parts of the pattern will exhibit intensity and position variations in response to the aforementioned averaging of the diffraction from the individual objects.

Figure 2:
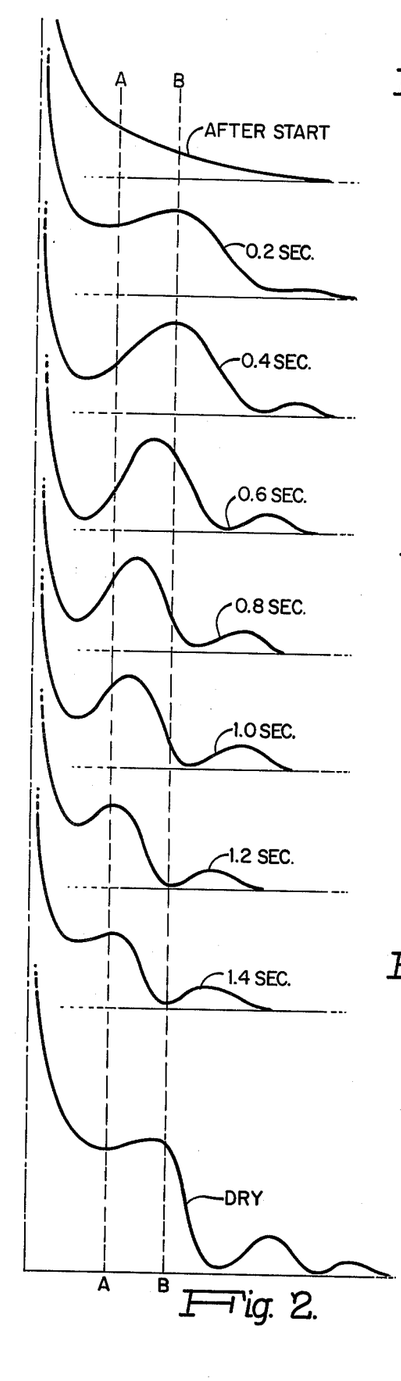
FIG. 2 is a diagrammatic representation of a radial portion of the diffraction pattern as it developes during the spinning process.

The pattern development process is illustrated in FIG. 2. Only half the pattern is illustrated because the pattern is symetrical about the incident beam. The sequential diffraction patterns depicted in FIG. 2 were produced by spinning a blood film without stopping at the point which would produce ideal cell spacing in order that the development of the pattern at longer spin times could be observed. In normal operation, a stop signal is generated after about 0.8 seconds of spinning, and the motor and platen stop rotating at about 1.1 or 1.2 seconds, long before drying commences.

If a cell monolayer density with a certain average cell spacing is desired, one can observe the developing diffraction pattern during a spin, as shown in FIG. 2, and indentify a particular part of the pattern that exhibits a rapid change in intensity at the time when the spinning should terminate. This can be done using high speed cinematography or stop frame videotape recording of the dynamic diffraction pattern.

Once the desired portion of the diffraction pattern has been identified, a photosensor can be positioned with respect to the diffraction pattern so that the particular portion of the pattern can be sensed to terminate the spinning operation. The output from the photosensor can be compared with a predetermined signal level to determine when spinning should cease. However, in order to reduce the affect of power and light source variations on the spin time, it is preferable to compare the primary photosensor output to a second photosensor which senses the light source intensity. Alternatively, a second photosensor can be placed in another portion of the diffraction pattern in which the intensity of the diffraction pattern undergoes a rapid change in the opposite direction to that of the primary photosensor. This latter arrangement can be used not only to reference the primary photosensor against light variations but also to increase accuracy of the termination point.

Figure 3A:
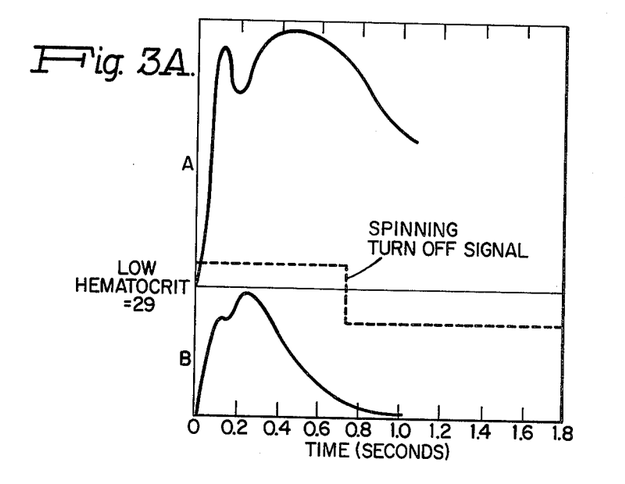
FIGS. 3A, 3B and 3C are plots of oscillagraphic traces showing the temporal relationship of the diffraction pattern sensor output and the spinning turn off signal for low hematocrit, normal hematocrit and high hematocrit blood respectively
Figure 3B:
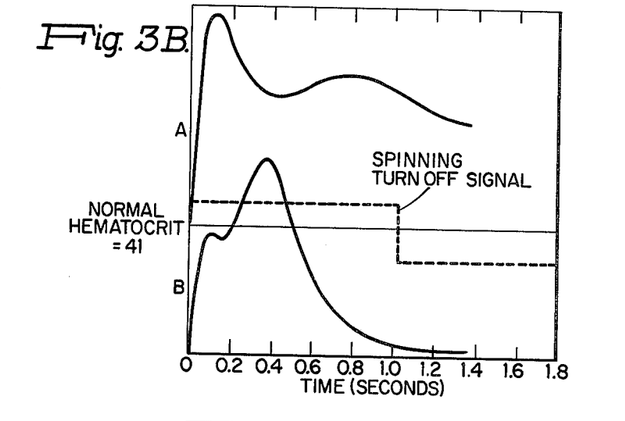
Figure 3C:
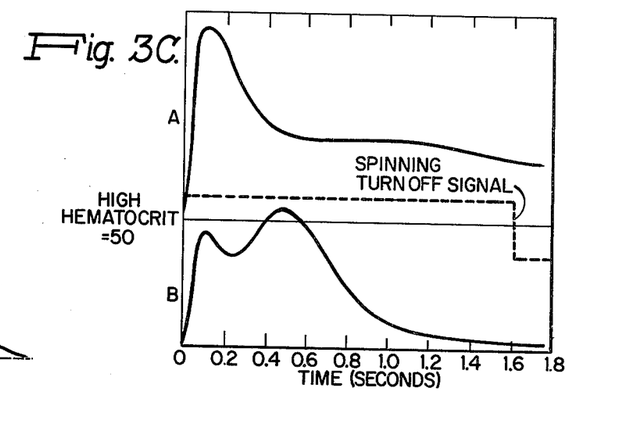

The time varying signals from two photosensors "A" and "B" are illustrated in FIGS. 3A, 3B and 3C. The photosensor signals from three varying hematocrits are depicted. The interaction of the two photosensor signals in varying the spinning time can be seen.

Having described the method of the invention, I will now describe various embodiments for implementing the method.

Figures 4, 5, 6:
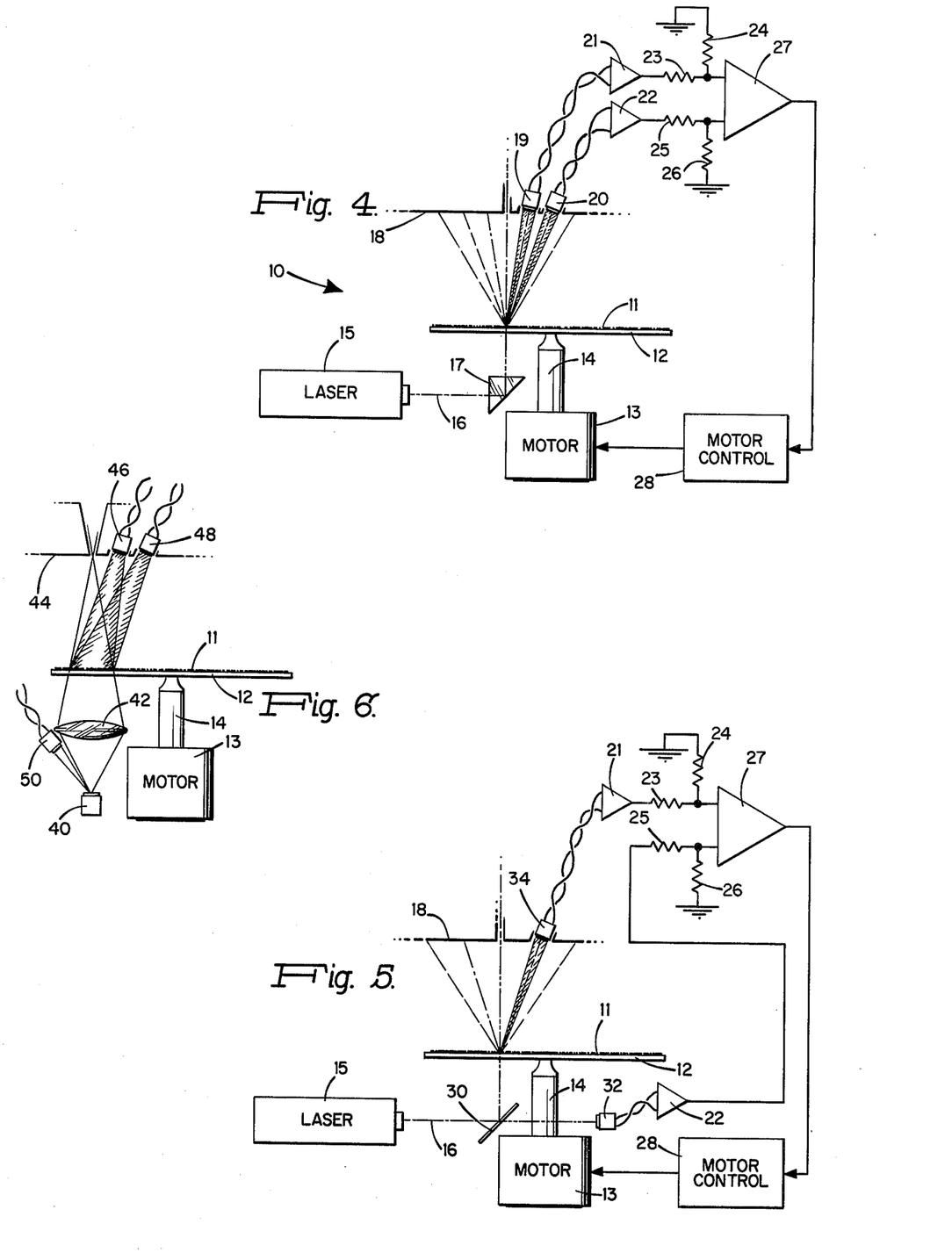
FIG. 4 is a diagrammatic illustration of the mechanical, electrical and optical elements of one embodiment of the invention in which two diffraction pattern detectors are employed.
FIG. 5 is a diagrammatic illustration of the mechanical, electrical and optical elements of another embodiment of the invention utilizing a simple off-axis diffraction pattern detector employed in conjunction with an incident light detector.
FIG. 6 is a diagrammatic illustration of the mechanical, electrical and optical elements of still another embodiment of the invention using anon-collimated light source.

FIG. 4 is a diagrammatic representation of a cell density control system constituted in accordance with the present invention and indicated generally by the reference numeral 10. A cell suspension 11 is placed on a transparent substrate 12 that is attached to motor 13 by means of motor shaft 14. The motor rotates rapidly causing centrifugal removal of a portion of the cell suspension.

A laser 15 produces a beam of coherent, collimated, quasi-monchromatic light 16. The light beam is directed to the substrate by prism 17 and passes through the cell suspension forming a diffraction pattern at a measuring plane 18. The incident beam passses through the measuring plane. Two photodetectors 19 and 20 are mounted at two different radially spaced positions in the diffraction pattern. The electrical output signals from the photodetectors are amplified by followers 21 and 22. The outputs from follower 21 and 22 are ratioed through resistors 23-24 and 25-26, respectively, and then compared in comparator 27. When the ratio of the signals reaches a predetermined value, indicating that the cell density has reached the desired value, the signal in the comparator 27 changes sign. This change in sign is sensed by motor control 28 which causes the motor 13 to stop. The specific circuitry for motor control 28 is not shown in detail because such circuits are well known to those skilled in the art, and are commercially available from a number of sources.

An alternative embodiment of the invention is snown in FIG. 5. As in FIG. 4, the particle or cell suspension 11 is spread on a transparent substrate 12 which is connected to motor 13 by shaft 14. The laser 15 produces a beam of collimated light 16 which is reflected by a partially silvered mirror 30 to illuminate the cell suspension. A small portion of the laser's beam is transmitted through mirror 30 to a reference photosensor 32. A position of the light diffracted by the particle suspension 11 is sensed by a single diffraction pattern photosensor 34. The output signals from the two photosensors are amplified by followers 21 and 22, ratioed by resistors 23-24, and 25-26 and then compared by comparator 27. When the proper cell spacing is achieved, comparator 27 produces a stop signal which causes motor control 28 to terminate the spinning of motor 13.

It is not necessary to use a collimated light source such as a laser. Referring to FIG. 6, non-collimated, non-coherent light source 40 can be used in combination with a lens 42. Since the diffraction pattern will appear in focus at only one plane 44, the photosensors 46 and 48 preferably are positioned at this plane of focus. Alternatively, as is illustrated in FIG. 6, instead of one of the diffraction pattern sensors 46 or 48, a reference sensor 50 can be used in conjunction with a single diffraction pattern sensor as illustrated in FIG. 5. The reference sensor 50 measures the magnitude of the incident light from the light source. For simplicity, the electronic circuits have not been repeated in FIG. 6 because they are identical with those shown in FIGS. 4 and 5.

If desired, the diffraction pattern energy level detected by photosensor 34 can be referenced to a preselected energy level that is independent of the cell density of the suspension and independent of the energy that is incident upon the suspension. In this case, the output from follower 21 is inputted to comparator 27 along with a preselected voltage level that is substituted for the output of follower 22 in FIG. 5.

In addition, it is not necessary that the incident light beam intersect the transparent substrate and particle suspension at a right angle as is illustrated in the preceding figures. However, if the angle of incidence is not 90°, the diffraction pattern will be elliptical rather than circular, and the positioning of the photosensors will necessarily have to take this into account.

Figure 7A:
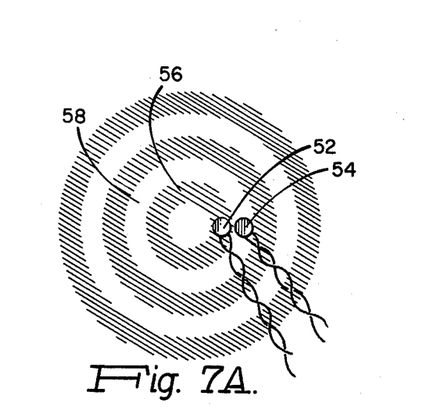
FIG. 7A is a diagrammatic representation of a circular diffraction pattern showing the position of two spot sensors.
Figure 7B:
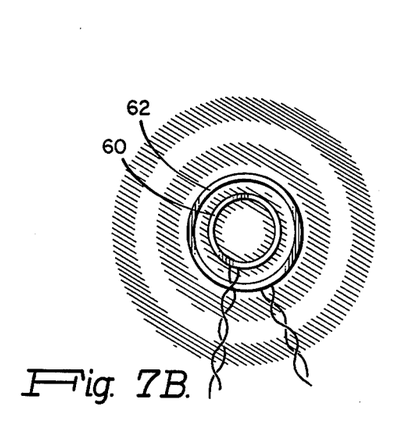
FIG. 7B is another diagrammatic representation of a circular diffraction pattern showing the position of two ring sensors; and, FIG. 8 is a view in perspective and partially broken away of a spinner chuck.

Referring now to FIGS. 7A and 7B which show two diagrammatic representations of circular diffraction patterns, spot sensors 52 and 54 can be used to detect the intensity of the first dark ring 56 and the first bright ring 58 of the pattern, respectively. However, since only a small portion of the energy in the ring is detected by such a small sensor, a very intense light source is needed to produce sufficient intensity in the diffraction pattern. Alternatively, more of the energy of the ring can be collected by using ring sensors 60 and 62 with a concomitant reduction in the intensity of the light source. The ring sensors 60 and 62 are depicted in FIG. 6 as very narrow for purposes of illustration. However, in practice the ring sensors would be somewhat wider, and could be considerably wider, encompassing more than one diffraction ring. Although, full circular ring sensors have been shown in FIG. 7B, it will be appreciated that one or more segmented arcuate sensors can be employed to increase the sensor signal output level over a single spot sensor for a given diffraction pattern intensity.

Figure 8:
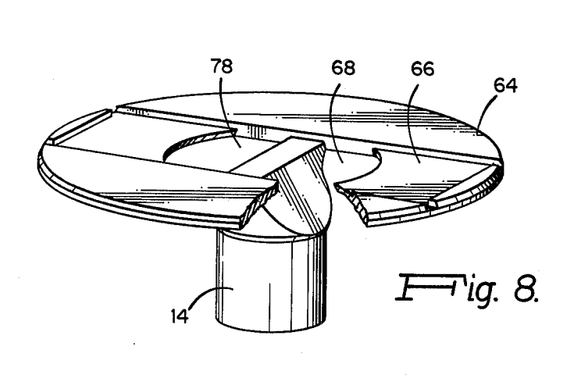

The transparent substrate 12 in FIG. 4 is shown attached to the motor shaft 14 directly. For the blood cell embodiment of the invention in which standard 25mm × 75mm microscope slides are used, it is convenient to utilize a platen 64 to hold the slide during spinning. The platen is attached to the motor shaft and is shown in detail in FIG. 8. The platen 64 has a depressed central area 66 for receiving a standard slide (not shown). Apertures 68 and 70 are provided to allow the light beam to impinge upon the slide.

During the first 200 msec. to 400 msec. of spinning, it is desirable to disable the motor stop function in order to allow the sensor signals to stabilize. In addition, once the motor conrol circuit has signaled that spinning has sufficiently separated the cells, it is also desirable to prevent the circuit from commanding further spinning because of signal variations as motor rotation ceases. For these reasons, it is preferable to include circuitry to prevent motor stopping for at least 200 msec. after starting, and to prevent immediate restarting after the stop signal.

Calibration of the photosensors is readily accomplished in the present invention. Using a well-spun, dry slide, the radial position of the photosensors is adjusted until the outer sensor detects the maximum intensity of the first bright ring (shown as B in FIG. 2 on the dry film curve). The inner sensor is then adjusted so that it is in the minimum between the incident beam and the first bright ring (shown as A in FIG. 2 on the dry film curve).

Having described in detail various preferred embodiments of my invention, it will now be apparent to those skilled in the art that numerous modification can be made therein without departing from the scope of the invention as defined in the following claims.

What I claim and desire to secure by Letters Patent of the United States is:

1. A method for producing a desired cell density in a suspension of biological cells on a substrate, said method comprising the steps of:
    (1) forming by electro-magnetic energy incident upon said cell suspension a cell modified pattern of electro-magnetic energy with respect to the axis of the incident electro-magnetic energy;
    (2) detecting electro-magnetic energy levels at at least one off-axis location in said cell modified electro-magnetic energized pattern; and
    (3) reducing the cell density of said suspension of biological cells until a predetermined energy level is detected at said at least one off-axis location, said detected energy level being referenced to a preselected, constant energy level which is independent of the cell density of the suspension.

2. The method of claim 1 further comprising the steps of reducing the thickness of said suspension of biological cells by rotating the substrate whereby centrifugal force causes a portion of the biological cell suspension to be removed from the substrate.

3. A method for producing a desired cell density in a suspension of biological cells on a substrate, said method comprising the steps of:

(1) forming by electro-magnetic energy incident upon said suspension a cell modified pattern of electro-magnetic energy with respect to the axis of the incident electro-magnetic energy;

(2) independently detecting electro-magnetic energy levels at a plurality of predetermined off-axis locations in said cell modified electro-magnetic pattern; and, (3) reducing the cell density of said suspension of biological cells until a predetermined pattern of electro-magnetic energy levels is detected at said off-axis locations in the cell modified electro-magnetic pattern.

4. The method of claim 3 further comprising reducing the thickness of said suspension of biological cells by rotating the substrate whereby centrifugal force causes a portion of the biological cell suspension to be removed from the substrate.

5. A method for producing a desired cell density in a suspension of biological cells on a substrate, said method comprising the steps of:

(1) forming by light incident upon said cell suspension, a diffraction pattern of the cell suspension, said diffraction pattern being positioned with respect to the axis of the incident light;

(2) independently detecting light energy levels at a plurality of predetermined off-axis locations in said diffraction pattern; and (3) reducing the cell density of said suspension of biological cells until a predetermined pattern of light energy levels is detected at said off axis locations in the diffraction pattern.

6. The method of claim 5 further comprising reducing the thickness of said suspension of biological cells by rotating the substrate whereby centrifugal force causes a portion of the biological cell suspension to be removed from the substrate.

7. The method of claim 5 wherein said light energy levels are independently detected at two off-axis locations in the diffraction pattern, said locations being selected to provide a maximum and opposite rate-of-change in light energy levels at the two locations when the cell density reaches the desired density.

8. The method of claim 5 wherein said light energy levels are independently detected at two off-axis locations in the diffraction pattern with one location being on a maximum light energy level in the pattern and the other location being on a minimum light energy level in the pattern when the cell density reaches the desired density.

9. A method for producing a desired cell density in a suspension of biological cells on a substrate; said method comprising the steps of:
   (1) rotating a substrate having thereon a suspension of biological cells at a speed sufficient to produce centrifugal removal of a portion of the biological cell suspension from the substrate;
   (2) forming by light incident upon said rotating substrate and blood cell suspension a diffraction pattern of the cell suspension, said diffraction pattern being positioned with respect to the axis of the incident light;
   (3) indpendently detecting light energy levels at a plurality of predetermined off-axis locations in said diffraction pattern; and,
   (4) terminating the rotation of said substrate and biological cell suspension when a predetermined pattern of light energy levels is detected at said off-axis locations in the diffraction pattern.

10. The method of claim 9 further comprising the steps of forming a circular diffraction pattern and independently detecting said light energy levels at at least two locations in the diffraction pattern, said locations being spaced at different radial distances from the axis of the incident light.

11. The method of claim 10 further comprising said at least two energy level detector locations being positioned along a radius from the axis of the incident light.

12. The method of claim 10 further comprising said at least two locations being circumferentially spaced with respect to the axis of the incident light.

13. The method of claim 9 wherein said light energy levels are independently detected at two off-axis locations in the diffraction pattern, said locations being selected to provide a maximum and opposite rate-of-change in light energy levels at the two locations when the cell density reaches the desired density.

14. The method of claim 9 wherein said light energy levels are independently at two off-axis locations in the diffraction pattern with one location being on a maximum light energy level in the pattern and the other location being on a minimum light energy level in the pattern when the cell density reaches the desired density.

15. The method of claim 9 further comprising the steps of forming an elliptical diffraction pattern and independently detecting said light energy levels at at least two locations in the diffraction pattern, said locations being spaced from the incident light axis by different distances as measured along one axis of the elliptical diffraction pattern.

16. An apparatus for producing a desired cell density in a suspension of biological cells on a substrate, said apparatus comprising:
   (1) means for forming by electro-magnetic energy incident upon said cell suspensiona cell modified pattern of electro-magnetic energy with respect to the axis of the incident electro-magnetic energy;
   (2) means for detecting electro-magnetic energy levels at at least one off-axis location in said cell modified electro-magnetic energy pattern; and,
   (3) means for reducing the cell density of said suspension of biological cells until a predetermined energy level is detected at said at least one off-axis location, said detected energy level being referenced to a preselected, constant energy level which is independent of the cell density of the suspension.

17. An apparatus for producing a desired cell density in a suspension of biological cells on a substrate, said apparatus comprising:
   (1) means for forming by electro-magnetic energy incident upon said cell suspension a cell modified pattern of electro-magnetic energy with respect to the axis of the incident electro-magnetic energy;
   (2) means for independently detecting electro-magnetic energy levels at a plurality of predetermined off-axis locations in said cell modified electro-magnetic energy pattern; and,
   (3) means for reducing the cell density of said suspension of biological cells until a predetermined pattern of electro-magnetic energy levels is detected at said off-axis locations in the cell modified electro-magnetic energy pattern.

18. An apparatus for producing a desired cell density in a suspension of biological cells on a substrate, said apparatus comprising:

(1) means for forming by light incident upon said cell suspension, a diffraction pattern of the cell suspension, said diffraction pattern being positioned with respect to the axis of the incident light;

(2) means for independently detecting light energy levels at a plurality of predetermined off-axis locations in said diffraction pattern; and (3) means for reducing the cell density of said suspension of biological cells until a predetermined pattern of light energy levels is detected at said off-axis locations in the diffraction pattern.

19. The apparatus of claim 18 wherein said light energy level detecting means detects light energy levels at two off-axis locations in the diffraction pattern, said locations being selected to provide a maximum and opposite rate-of-change in light energy levels at the two locations when the cell density reaches the desired density.

20. The apparatus of claim 18 wherein said light energy level detecting means detects light energy levels at two off-axis locations in the diffraction pattern with one location being on a maximum light energy level in the pattern and the other location being on a minimum light energy level in the pattern when the cell density reaches the desired density.

21. An apparatus for producing a desired cell density in a suspension of biological cells on a substrate, said apparatus comprising:
(1) means for rotating a substrate having thereon a suspension of biological cells at a speed sufficient to produce centrifugal removal of a portion of the biological cell suspension from the substrate;
(2) means for forming by light incident upon the substrate and biological cell suspension a diffraction pattern of the cell suspension, said diffraction being positioned with respect to the axis of the incident light;
(3) means for independently detecting light energy levels at a plurality of predetermined off-axis locations in said diffraction pattern; and,
(4) means for terminating the rotation of the substrate and cell suspension by said rotating means when a predetermined pattern of light energy levels is detected at said off-axis locations in the diffraction pattern.

22. The apparatus of claim 21 wherein said means for forming a diffraction pattern includes a laser for illuminating the cell suspension and substrate with an incident beam of coherent collimated, substantially monochromatic light.

23. The apparatus of claim 21 wherein said substrate is transparent and said means for forming a diffraction pattern includes a light source and optical means for forming an image of said light source at a location beyond the substrate on one side thereof when the light source is located on the other side of the substrate.

24. The apparatus of claim 23 wherein said light source image is formed at an image plane and wherein said means for independently detecting light energy levels is located at said image plane.

25. The apparatus of claim 21 wherein said light energy level detecting means detects light energy levels at two off-axis locations in the diffraction pattern with one location being on a maximum light energy level in the pattern and the other location being on a minimum light energy level in the pattern when the cell density reaches the desired density.

26. The apparatus of claim 25 wherein said two locations in the diffraction pattern are the first bright ring and the first dark ring of the diffraction pattern when the cell density reaches the desired density.

27. The apparatus of claim 21 wherein said diffraction pattern forming means forms a circular diffraction pattern and wherein said light energy level detecting means detects light energy levels at at least two locations in the diffraction pattern which are spaced at different radial distances from the center of the pattern.

28. The apparatus of claim 27 wherein said at least two locations are circumferentially spaced with respect to the center of the diffraction pattern.

29. The apparatus of claim 27 wherein said at least two locations are located along a radius of the circular diffraction pattern.

30. A method for producing a desired cell density in a suspension of biological cells on a substrate, said method comprising the steps of:
(1) forming by electro-magnetic energy incident upon said cell suspension a cell modified pattern of electro-magnetic energy with respect to the axis of the incident electro-magnetic energy;
(2) detecting electro-magnetic energy levels at at least one off-axis location in said cell modified electro-magnetic energized pattern; and,
(3) reducing the cell density of said suspension of biological cells until a predetermined energy level is detected at said at least one off-axis location, said detected energy level being referenced to an energy level which is a function of the energy incident upon said cell suspension and which is independent of the cell density of the suspension.

31. The method of claim 30 further comprising the step of reducing the thickness of said suspension of biological cells by rotating the substrate whereby centrifugal force causes a portion of the biological cell suspension to be removed from the substrate.

32. An apparatus for producing a desired cell density in a suspension of biological cells on a substrate, said apparatus comprising:
(1) means for rotating a substrate having thereon a suspension of biological cells at a speed sufficient to produce centrifugal removal of a portion of the biological cell suspension from the substrate;
(2) means for forming by light incident upon the substrate and biological cell suspension a diffraction pattern of the cell suspension, said diffraction being positioned with respect to the axis of the incident light;
(3) means for independently detecting light energy levels at two preselected off-axis locations in the diffraction pattern, said locations being selected to provide a maximum and opposite rate-of-change in the light energy levels at the two locations when the cell density reaches the desired density; and,
(4) means for terminating the rotation of the substrate and cell suspension by said rotating means when a predetermined pattern of light energy levels is detected at said off-axis locations in the diffraction pattern.

33. An apparatus for producing a desired cell density in a suspension of biological cells on a substrate, said apparatus comprising:
(1) means for forming by electro-magnetic energy incident upon said cell suspension a cell modified pattern of electro-magnetic energy with respect to the axis of the incident electro-magnetic energy;
(2) means for detecting electro-magnetic energy levels at at least one off-axis location in said cell modified electro-magnetic energy pattern; and,
(3) means for reducing the cell density of said suspension of biological cells until a predetermined energy level is detected at said at least one off-axis location, said detected energy level being referenced to an energy level which is a function of the energy incident upon said cell suspension and which is independent of the cell density of the suspension.

34. An apparatus for producing a desired cell density in a suspension of biological cells on a substrate, said apparatus comprising:
(1) means for rotating a substrate having thereon a suspension of biological cells at a speed sufficient to produce centrifugal removal of a portion of the biological cell suspension from the substrate;
(2) means for forming by light incident upon the substrate and biological cell suspension an elliptical diffraction pattern of the cell suspension, said diffraction being positioned with respect to the axis of the incident light;
(3) means for independently detecting light energy levels at at least two off-axis locations in the diffraction pattern, said location being spaced from the incident light axis by different distances as measured along one axis of the elliptical diffraction pattern; and, (4) means for terminating the rotation of the substrate and cell suspension by said rotating means when a predetermined pattern of light energy levels is detected at said off-axis locations in the diffraction pattern.

35. The apparatus of claim 34 wherein two of said off-axis locations are selected to provide a maximum and opposite rate-of-change in light energy levels at the two locations when the cell density reaches the desired density.

36. The apparatus of claim 34 wherein two of said off-axis locations are located in the diffraction pattern with one location being on a maximum light energy level in the pattern and the other location being on a minimum light energy level in the pattern when the cell density reaches the desired density.

* * * * *